United States Patent [19]

Neier et al.

[11] Patent Number: 4,476,333
[45] Date of Patent: Oct. 9, 1984

[54] PROCESS FOR THE CONTINUOUS PRODUCTION OF SECONDARY BUTYL ALCOHOL

[75] Inventors: Wilhelm Neier; Werner Webers, both of Rheinberg; Rainer Ruckhaber, Moers; Günther Osterburg, Duisburg; Wolf J. Ostwald, Rheinberg, all of Fed. Rep. of Germany

[73] Assignee: Deutsche Texaco Aktiengesellschaft, Hamburg, Fed. Rep. of Germany

[21] Appl. No.: 461,363

[22] Filed: Jan. 27, 1983

Related U.S. Application Data

[63] Continuation-in-part of Ser. No. 312,205, Oct. 19, 1981, abandoned.

[30] Foreign Application Priority Data

Oct. 31, 1980 [DE] Fed. Rep. of Germany ....... 3040997

[51] Int. Cl.³ .............................................. C07C 29/04
[52] U.S. Cl. ................................... 568/899; 568/403
[58] Field of Search ......................................... 568/899

[56] References Cited

U.S. PATENT DOCUMENTS 2,144,750  1/1939  Bent ..................................... 568/899
3,994,983  11/1976  Webers .............................. 568/899

Primary Examiner—J. E. Evans
Attorney, Agent, or Firm—Robert A. Kulason; James F. Young; James J. O'Loughlin

[57] ABSTRACT

A process for the production of secondary butyl alcohol by the direct hydration of n-butenes in the presence of an acidic cation exchange resin catalyst which comprises depressurizing the vaporous product stream from a reactor to a pressure ranging from 15 to 40 bar and cooling the depressurizing product stream to a temperature of 120° C. or below to liquefy the product stream, separating an aqueous fraction from said stream leaving an alcohol-butene/butane organic mixture, vaporizing said organic mixture, depressurizing said organic mixture to a pressure ranging from 3 to 30 bar and including a pressure of from 3 to 8 bar and introducing said depressurized organic mixture into a separation column to separate secondary butyl alcohol from said mixture.

10 Claims, 1 Drawing Figure

PROCESS FOR THE CONTINUOUS PRODUCTION OF SECONDARY BUTYL ALCOHOL

BACKGROUND OF THE INVENTION

This application is a continuation-in-part of U.S. application Ser. No. 312,205 filed on Oct. 19, 1981, now abandoned.

FIELD OF THE INVENTION

This invention relates to the production of secondary butyl alcohol by the catalytic hydration of n-butenes in the presence of strongly acidic cation exchange resin catalysts.

DESCRIPTION OF THE PRIOR ART

A process for the continuous production of lower alcohols wherein the vaporous alcohol is removed overhead from the reactor together with excess reaction gas and more than 80% alcohol is obtained after the removal of the gas portion is known. According to this process, the alcohol may be obtained either by intermediate pressure release in a separating system as described in DE-AS No. 24 29 770 or by separation in a pressurized column (stabilizer column) operated in a conventional manner. In both cases, the secondary butyl alcohol obtained has a water content ranging from 15 to 23% depending on the cross-sectional gas load. This alcohol cannot be charged to the dehydrogenating reactor without prior drying as by distillation with benzene in the conventional way.

It is an object of this invention to provide a process for the production of secondary butyl alcohol by the hydration of n-butenes in a sump reactor so that after separation of a gas phase from the alcohol, a crude alcohol can be obtained which contains only a small amount of water together with the ether formed. Such a crude secondary butyl alcohol having a concentration of about 99% secondary butyl alcohol can be directly charged to a dehydrogenating reactor for the production of methyl ethyl ketone without the necessity of an intermediate distillation step.

SUMMARY OF THE INVENTION

The process of this invention is directed to a method for producing a secondary butyl alcohol from the direct hydration reaction of butenes with water in the presence of an acidic cation exchange resin catalyst resulting in the production of a product stream comprising secondary butyl alcohol, water, unreacted butenes and butane at a temperature ranging from about 120° C. to 180° C. under a pressure of approximately 40 to 200 bar which comprises reducing the pressure of the product stream to a pressure ranging from about 15 to 40 bar and cooling the product stream to a temperature of 120° C. or lower to liquefy the product stream, separating an aqueous fraction from said product stream leaving an organic mixture comprising secondary butyl alcohol, butenes, butane and water, vaporizing said mixture, depressurizing said mixture to a pressure ranging from 3 to 30 bar and including a pressure of from 3 to 8 bar, and introducing said depressurized organic mixture into a separation column to separate a liquid fraction comprising secondary butyl alcohol. Unreacted butenes are recycled to the feed to the direct hydration reactor.

DETAILED DESCRIPTION OF THE INVENTION

Figure 1:
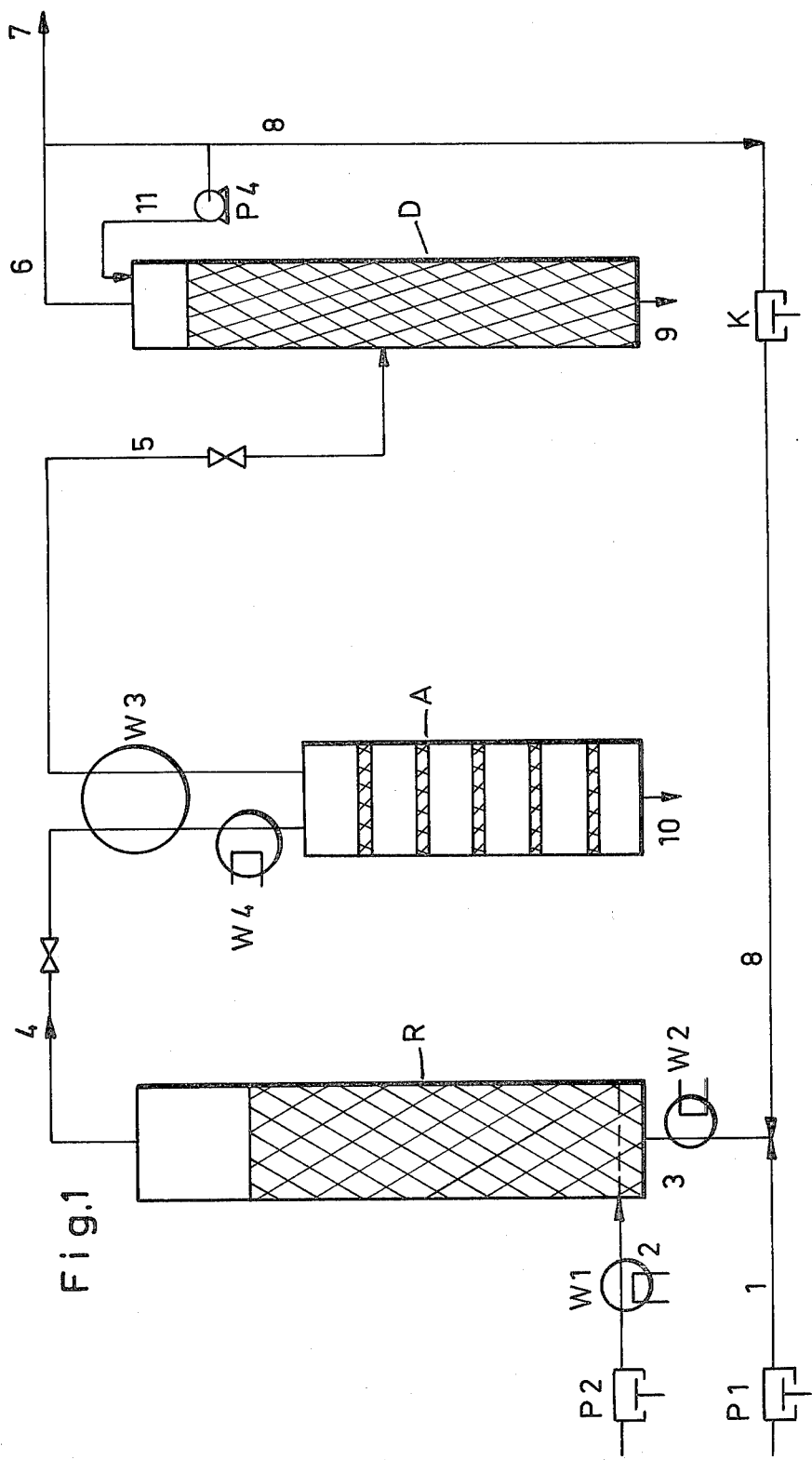

More specifically, the process of this invention is directed to an improved process for recovering secondary butyl alcohol from the product stream resulting from the direct hydration of a butene/butane hydrocarbon fraction with water in the presence of an acid acting catalyst. In general, the direct hydration reaction is conducted at a temperature ranging from above 120° C. to 180° C. under a pressure of approximately 40 to 200 bar employing a water to olefin mole ratio ranging from about 0.5 to 10 moles of water per mole of butene in the presence of a strongly acidic cation exchange resin catalyst. The reactants are passed through a reactor containing a fixed bed of the cation exchange resin catalyst in an upflow direction. The reaction product issuing from the top of the reactor is at approximately the same temperature and pressure as that employed in the reactor and comprises a mixture of secondary butyl alcohol, water, unreacted butenes and butane from the olefin feed stream.

In accordance with the process of the invention, the vaporous product stream comprising secondary butyl alcohol, water, unreacted butene and butane at a temperature in the range above 120° C. to 180° C. and under a pressure from about 40 to 200 bar is depressurized to a pressure in the range of 15 to 40 bar, and, more particularly, to a pressure of about 30 bar. Simultaneously or sequentially, the product stream is cooled to a temperature in the range of 10° to 120° C., preferably to a temperature ranging from about 80° to 120° C. to condense or liquify the product stream. An aqueous fraction containing about 90% of the water present in the product stream from the reactor is separated from the product stream in a separator, such as a demisting column, leaving a mixture comprising secondary butyl alcohol, unreacted butenes, butane and a minor amount of water. This mixture is vaporized and then depressurized to a pressure ranging from 3 to 30 bar and including a pressure of from about 3 to 8 bar to form a liquid fraction comprising secondary butyl alcohol. The secondary butyl alcohol fraction is separated and a gas mixture comprising unreacted butenes and butane is recycled to the olefin feed stream to the direct hydration catalytic reactor.

FIG. 1 illustrates the process of the invention. Using a dosing pump, P1, the feedgas from line 1 is mixed with the recycled olefin from line 8, is vaporized in evaporator W 2, and is charged through line 3 to the sump of reactor (R). Using pump P 2, the reaction water is fed to the reactor through line 2 after preheating in heat exchanger W 1. The reactor is packed with a strongly acidic ion exchange resin based on styrene/divinyl benzene. Both reaction components are led through the reactor bed in upstream operation. From the top of the reactor a small stream of water may be removed (not shown in the figure). The total amount of vaporous alcohol formed is removed overhead from the reactor through line 4 together with excess reaction gas (n-butane/n-butenes), is cooled and liquified while maintaining or lowering the pressure, and is led via heat exchanges W 3 and W 4 through a separation (A) provided with demister nettings. The separated water containing only small amounts of alcohol (<1%) is removed through line 10 and recycled to line 2 from where it is recharged as process water. The liquid alcohol-butenes/butane mixture is vaporized again by exchange in heat exchanger W 3 and transferred through line 5 to a pressurized column (D) where it is split into alcohol (line 9) and reaction gas (line 6). Using pump P 4 a small reflux (11) is charged to the column. Most of the the reaction gas is recycled through line 8 to the reaction using compressor (K). From line 7, a small amount of residual gas is removed.

According to the present invention, most of the water discharged together with the gas can be separated by cooling under pressure the product gas stream leaving the reactor to 135° C. or lower temperatures. In the subsequent separation of residual gas by distillation—in the case of the production of secondary butyl alcohol in the separation of butane/butenes mixture—the alcohol obtained has a water content of appreciably less than 0.1%, such as 0.005 to 0.05%. This alcohol can be directly used in the dehydrogenation to ketone without any further treatment.

Another advantage of intermediate cooling or intermediate condensation is that the reflux ratio in the stabilizer column can be lowered from 1.3 to 0.3. Thus, energy savings of approximately 43% for this column are attained. Since the energy consumption of this column makes up a considerable amount of the total energy requirement, the energy savings for this column are of great importance.

Cooling can also be performed at lower temperatures, e.g. at −10° C. or −20° C. However, this procedure is much more expensive and would normally not be advisable from the economical point of view. Preferably, the product gas stream is cooled and liquefied and the liquid alcohol/gas mixture leaving a separator is heated and vaporized simultaneously by means of a heat exchanger (heat exchanger W 3).

Examples I and II below illustrate prior art processes as described in DE-AS No. 24 29 770, wherein two separators are employed (Example I) and where a single pressurized column is employed (Example II).

EXAMPLE I (Prior Art)

An upright stainless steel tube reactor (inside diameter 26 mm, length 3 meters) was packed up to a height of 2.83 meters with 1.5 liters of Raschig rings (stainless steel, 4×4 mm) ad subsequently up to the same height with 1.2 liters of a commercial macroporous cation exchange resin (sulfonated styrene/divinyl benzene mixed polymerizate) in the $H^{(+)}$-form. This packing material/catalyst fixed bed was held by stainless steel netting arranged above and below the bed.

To the bottom of the tube reactor 232 grams of an 87% n-butenes mixture (3.6 moles of n-butenes) and 58 grams (3.2 moles) of water were charged per hour. Using a heating jacket, a temperature of 150° C. and a pressure of 70 bar were maintained in the reactor.

From the gas space in the reactor head, the vaporous reaction product was removed. Part of the product was recycled to the reactor using a circulating pump and was mixed thereby with recycled residual gas and feedgas to obtain an approximate 78 to 81% n-butenes containing mixed gas.

After depressuring the other portion of the vaporous reaction product to 25 to 30 bar, the product was charged to a first separator where after separation of $C_4$-residual gas a liquid crude alcohol was obtained which was depressurized to normal pressure in a second separator.

The residual gas containing 76% n-butenes (gas conversion relative to feed gas = 52.6%) was led from the first separator (pressure separator) to a compressor where it was compressed to 70 bar and from where it was recycled to the reactor, namely together with the recycle stream and the 87% feed gas stream in the form of a 78 to 81% n-butenes containing mixed gas.

From the recycle, a 76% residual gas containing 95.2 grams of n-butenes (1.7 moles) and 30.4 grams of n-butene (0.52 mole) was removed per hours, was depressured to normal atmospheric pressure in the second separator and was discharged. In the second separator 140 grams (1.9 moles) of secondary butyl alcohol and 0.7–1.4 grams of di-sec. butyl ether were obtained per hour after removing the $C_4$-components in the form of a 77 to 89% crude alcohol still containing 10–22% water. The space-time yield of secondary butyl alcohol was 1.6 moles per liter of catalyst an hour, the selectivity being more than 99%.

EXAMPLE II (Prior Art)

The product gas stream removed overhead from the reactor according to Example I was depressurized to 8 bar, charged to a pressurized column and split into secondary butyl alcohol and excess reaction gas. The excess reaction gas was recycled to the reactor as described before. A small part thereof was removed as residual gas. The same reaction conditions were employed and the same catalyst efficiency and selectivity was attained. The crude alcohol contained yet 15 to 10% water.

The following example illustrates the improved process of the invention.

EXAMPLE III

The process described in Examples I and II was altered in that the product stream comprising formed secondary butyl alcohol removed overhead from the reactor together with excess reaction gas was cooled to 100° C. at a pressure of 30 bar to liquefy the product stream. This liquid stream was passed through a separator packed with demister nettings. The separator was a pressurized tube (26 mm in diameter) packed with 6 demister netting layers each having a thickness of 50 mm. Between the individual demister nettings there were a free space of 100 mm each. At the bottom of the separator, approximately 90% of the water entrained with the secondary butyl alcohol-butenes/butane mixture was separated as a liquid fraction. This water phase contained only 0.6 to 0.8% secondary butyl alcohol and ether. From the top of the separator, a mixture of the reaction product, secondary butyl alcohol, some di-sec. butyl ether and excess reaction gas consisting of butenes and butane was vaporized by exchange in heat exchanger W3, depressured to 8 bar, and charged to a pressurized column. In this column, crude secondary butyl alcohol was separated as a liquid fraction from the reaction gas. The excess reaction gas was led through line 8 to the compressor, where it was recompressed and then recycled to the reactor. The crude alcohol obtained in the column sump contained not more than 0.01 to 0.05% water. Yield and selectivity were the same as in Example I.

The process of the invention wherein secondary butyl alcohol can be continuously produced relatively free of water represents a substantial and surprising improvement in the manufacture and recovery of this valuable product.

What is claimed is:

1. A process for the continuous production of secondary butyl alcohol by the catalytic hydration of n-butenes with water in the presence of a strongly acidic cation exchange resin catalyst in a fixed bed reactor by passing the reactants over a catalyst in upstream flow at a temperature ranging from above 120° C. to 180° C., a pressure from about 40 to 200 bar, and a water/olefin mole ratio ranging from about 0.5 to 10 moles of water per mole of n-butenes, which comprises producing a vaporous overhead product stream comprising water and an organic mixture comprising secondary butyl alcohol and unreacted reaction gases n-butenes and butane, depressurizing and cooling said product stream to a pressure ranging from about 15 to 40 bar and a temperature ranging up to about 120° C. to liquefy said product stream, introducing said liquefied product stream into a separator to form an aqueous bottoms fraction and a liquid organic mixture comprising secondary butyl alcohol and reaction gases n-butenes and butane, separating said aqueous bottoms fraction from said separator, vaporizing said organic mixture to form an overhead vaporized organic mixture, depressurizing said overhead vaporized organic mixture to a pressure ranging from 3 to 8 bar, introducing said depressurized overhead organic mixture into a pressurized column to form a liquid bottoms fraction comprising secondary butyl alcohol and a vaporous reaction gas fraction, and recovering said secondary butyl alcohol as a liquid crude alcohol bottoms fraction containing less than 0.1 percent water.

2. A process according to claim 1 in which said depressurized and cooled product stream is cooled to a temperature ranging from 80° to 120° C.

3. A process according to claim 1 in which said depressurized and cooled product stream is cooled to a temperature of about 100° C.

4. A process according to claim 1 in which said vaporized organic mixture is depressurized to a pressure of about 8 bar.

5. A process for the continuous production of secondary butyl alcohol by the catalytic hydration of n-butenes with water in the presence of a strongly acidic cation exchange resin catalyst in a fixed bed reactor by passing the reactants over a catalyst in upstream flow at a temperature ranging from above 120° C. to 180° C., a pressure from about 40 to 200 bar, and a water/olefin mole ratio ranging from about 0.5 to 10 moles of water per mole of n-butenes, which comprises producing a vaporous overhead product stream comprising water and an organic mixture comprising secondary butyl alcohol and unreacted reaction gases n-butenes and butane, depressurizing and cooling said product stream to a pressure ranging from about 15 to 40 bar and a temperature ranging from about 10° C. to 120° C. to liquefy said product stream, introducing said liquefied product stream into a separator to form an aqueous bottoms fraction and a liquid organic mixture comprising secondary butyl alcohol and reaction gases n-butenes and butane, separating said aqueous bottoms fraction from said separator, said aqueous bottoms fraction comprising appproximately 90% of the water entrained in said vaporous overhead product stream and containing less than 1 percent of secondary butyl alcohol, vaporizing said organic mixture to form an overhead vaporized organic mixture, depressurizing said overhead vaporized organic mixture to a pressure ranging from 3 to 8 bar, introducing said depressurized overhead organic mixture into a second separator to form a liquid bottoms fraction comprising secondary butyl alcohol and a vaporous reaction gas fraction, and recovering said secondary butyl alcohol as a liquid crude alcohol bottoms fraction containing less than 0.1 percent water.

6. A process according to claim 5 in which said depressurized and cooled product stream is cooled to a temperature ranging from 80° to 120° C.

7. A process according to claim 5 in which said depressurized and cooled product stream is cooled to a temperature of about 100° C.

8. A process according to claim 5 in which said vaporized organic mixture is depressurized to a pressure of about 8 bar.

9. A process for the continuous production of secondary butyl alcohol by the catalytic hydration of n-butenes with water in the presence of a strongly acidic cation exchange resin catalyst in a fixed bed reactor by passing the reactants over a catalyst in upstream flow at a temperature of about 150° C., a pressure of about 70 bar, and a water/olefin mole ratio ranging from about 0.5 to 10 moles of water per mole of n-butenes, which comprises producing a vaporous overhead product stream comprising water and an organic mixture comprising secondary butyl alcohol and unreacted reaction gases n-butenes and butane, depressurizing and cooling said product stream to a pressure of about 30 bar and a temperature ranging from about 80° to 120° C. to liquefy said product stream, introducing said liquefied product stream into a separator to form an aqueous bottoms fraction and a liquid organic mixture comprising secondary butyl alcohol and reaction gases n-butenes and butane, separating said aqueous bottoms fraction from said separator, said aqueous bottoms fraction comprising approximately 90% of the water entrained in said vaporous overhead product stream and containing less than 1 percent of secondary butyl alcohol, vaporizing said organic mixture to form an overhead vaporized organic mixture, depressurizing said overhead vaporized organic mixture to a pressure of about 8 bar, introducing said depressurized overhead organic mixture into a second separator to form a liquid bottoms fraction comprising secondary butyl alcohol and a vaporous reaction gas fraction, and recovering said secondary butyl alcohol as a liquid crude alcohol bottoms fraction containing less than 0.1 weight percent water.

10. A process according to claim 9 in which said vaporous reaction gas fraction is recycled to said reactor.

* * * * *